United States Patent
Ruohonen et al.

(10) Patent No.: US 6,537,197 B1
(45) Date of Patent: Mar. 25, 2003

(54) METHOD FOR PRODUCING ILLUSORY MAGNETIC STIMULATION

(75) Inventors: Jarmo Ruohonen, Helsinki (FI); Risto Ilmoniemi, Espoo (FI); Marko Ollikainen, Vantaa (FI); Juha Virtanen, Helsinki (FI)

(73) Assignee: Nexstim Oy, Helsinki (FI)

( * ) Notice: Subject to any disclaimer, the term of this patent is extended or adjusted under 35 U.S.C. 154(b) by 0 days.

(21) Appl. No.: 09/743,382
(22) PCT Filed: Jul. 1, 1999
(86) PCT No.: PCT/FI99/00587
§ 371 (c)(1), (2), (4) Date: Mar. 7, 2001
(87) PCT Pub. No.: WO00/02624
PCT Pub. Date: Jan. 20, 2000

(30) Foreign Application Priority Data

Jul. 10, 1998 (FI) .................................................. 981595

(51) Int. Cl.⁷ .............................. A61N 1/00; H01F 5/00
(52) U.S. Cl. ........................................... 600/13; 335/299
(58) Field of Search ............................... 600/9, 13–14, 600/27, 15; 335/299

(56) References Cited

U.S. PATENT DOCUMENTS

| | | | |
|---|---|---|---|
| 4,454,883 A | * 6/1984 | Fellus | 600/14 |
| 5,014,699 A | * 5/1991 | Pollack et al. | 600/13 |
| 5,895,348 A | * 4/1999 | Hosaka | 600/27 |
| 5,935,054 A | * 8/1999 | Loos | 600/9 |

* cited by examiner

Primary Examiner—Max F. Hindenburg
Assistant Examiner—Nikita R Veniaminov
(74) Attorney, Agent, or Firm—Smith-Hill and Bedell

(57) ABSTRACT

Disclosed is a method for producing a magnetic stimulation effect and/or a fake magnetic stimulation effect in a biological tissue. According to the method, the real magnetic stimulation is effected by virtue of inducing an electromagnetic field in said biological tissue with a sufficiently strong field strength to essentially excite said tissue, and the fake magnetic stimulation is effected by virtue of inducing an electromagnetic field in said biological tissue with a field strength that is weaker than the electromagnetic field required for an essential excitation of said tissue. According to the invention, said electromagnetic field weaker than the electromagnetic field strength required for an essential excitation of the tissue is produced by the steps of inducing at least one first electromagnetic field in said biological tissue and, simultaneously, inducing at least one second electromagnetic field superimposed with said first electromagnetic field but so deviated by its direction from the direction of said first electromagnetic that the sum effect of said electromagnetic fields in the target area of said biological tissue remains weaker than the electromagnetic field required for an essential excitation of said tissue. Also an apparatus is described suited for implementing the method.

15 Claims, 2 Drawing Sheets

METHOD FOR PRODUCING ILLUSORY MAGNETIC STIMULATION

Figure 1:
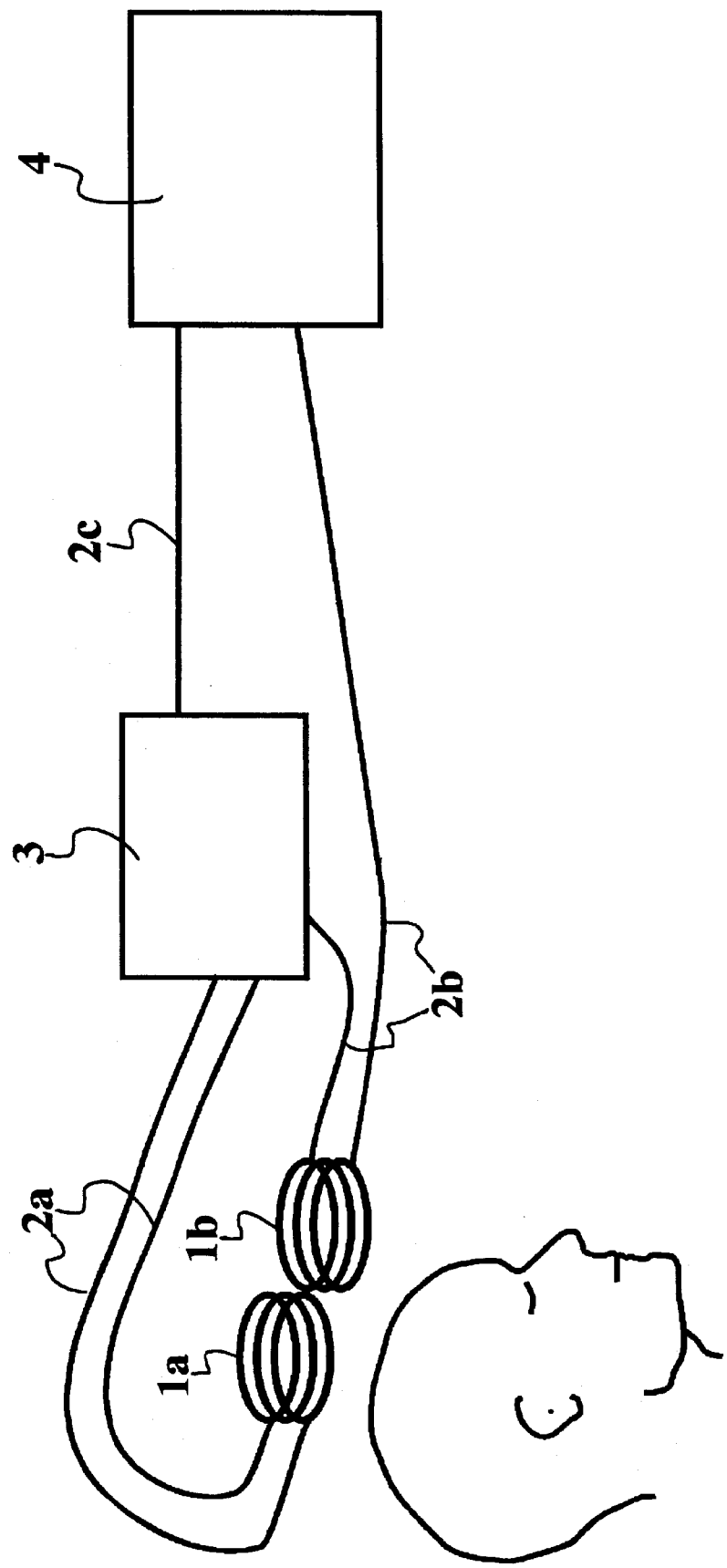

The present invention relates to a method for producing illusory magnetic stimulation.

The present invention relates to a method according to the preamble of claim 1.

Methods and apparatuses of the kind discussed herein are used for measuring and examining the response of biological tissue through stimulating the same by electro-magnetic means.

Using conventional techniques, it is possible to stimulate biological tissue such as the brain, the peripheral nervous system, muscles and the heart by virtue of inducing an electric field in the tissue. In magnetic stimulation, the induction of the electric field is provided by means of a changing magnetic field. Different types of apparatus constructions based on magnetic stimulation are described, e.g., in U.S. Pat. Nos. 4,940,453; 5,047,005; 5,061,234; 5,066,272 and 5,267,938 and FI Pat. No. 100,458.

Magnetic stimulators deliver the changing magnetic field by means of a coil. The coil transduces the electric energy fed by the power source of the stimulator into magnetic field energy. The coil can be an integral or separate part of a magnetic stimulator. Some practicable coil constructions are discussed, e.g., in U.S. Pat. Nos. 4,994,015; 5,078,674; 5,116,304 and 5,725,471.

Magnetic stimulation has been found a risk- and pain-free method of stimulating human brain, peripheral nervous system or muscles. The method has a plurality of applications in basic research, diagnosis and therapy.

Magnetic stimulation of the brain, however, also involves activation of skin on the skull. The electromagnetic field induced by the coil is weaker the greater the distance from the coil. Hence, when the electromagnetic field in the brain is brought sufficiently strong to excite the nerve cells, the field strength on the scalp is manyfold. This high-level excitation causes contraction of scalp muscles and activation of nerve ends on the skin, which is felt by the test person as a sensation resembling as a knock or pinch. The sensation may also be slightly painful if the stimulated area coincides with a greater mass of muscles. The sensations felt on the scalp cannot be eliminated by any conventional technique known in the art.

Magnetic stimulation by conventional techniques also includes a strong sonic bang that evokes an auditory sensation. This sound effect can be attenuated but not generally eliminated through the use of hearing protectors.

Both the stimulation of the scalp and the sonic bang emitted by the stimulation coil activate the sensory nerve paths leading to the brain and, thus, the brain areas associated with sensory information. This brain activation interferes with the magnetic stimulation of the brain evoked directly by the stimulating electromagnetic field. Therefore, it is often difficult to identify whether a given result of stimulation is caused by direct stimulation of the brain or evoked by the sensory feelings on the scalp and the sonic bang heard by the test person.

The contribution of scalp stimulation and the auditory evoked response related to the sonic bang emitted by the coil in the overall stimulated response can be estimated by producing fake pulses of magnetic stimulation and then measuring the effect of stimulation caused by these pulses. Herein, the term fake magnetic stimulation refers to stimulation that produces the same sensory and auditory stimulation as a real magnetic stimulation, yet inducing such a low field on the brain that cannot cause direct stimulation of nerve cells in the brain.

A typical test necessitating the use of fake magnetic stimulation is encountered in the examination of the brain of patients suffering from depression. Herein, it is impossible to tell in a reliable manner whether the detected effects are related to the multisensory response evoked by the magnetic stimulation or are they triggered by the stimulation of the brain tissue.

Fake magnetic stimulation by means of conventional techniques and methods is accomplished by moving or rotating the coil into different positions above the head so that the field induced over certain areas of the brain is diminished.

One problem hampering the conventional technique is that the coil must be moved or rotated for the fake stimulation, whereby switching between the real magnetic stimulation and the fake magnetic stimulation takes time from tens of seconds up to several minutes. Also the position of the coil in respect to the object being stimulated may change appreciably when moving or tilting the coil into the fake stimulation position and back therefrom.

Another problem of conventional technique is that the change of coil position and, thus, the change of stimulation method is relatively easy to detect by the test person.

It is an object of the invention to overcome the above-described disadvantages and to provide an entirely novel type of method and apparatus for producing fake magnetic stimulation.

The goal of the invention is achieved by producing the fake magnetic stimulation through the induction of at least two variable magnetic fields so that at least two of the magnetic fields are oriented in different directions, e.g., opposite to each other in the target area. The directions and magnitudes of the magnetic fields are set so as to attain partial cancellation of the electric fields, which are induced by the varying magnetic fields, within the target area such as the brain tissue, in a manner that avoids causing essential stimulation of the target area tissue by the direct effect of the fake stimulation field. The magnetic fields oriented in different directions can be produced using, e.g., two or a greater number of coils fed by varying currents. Alternatively, a suitable formed coil having, e.g., a figure-of-eight shape can be used. Notwithstanding the desired interior cancellation of the induced electromagnetic fields, the exterior field must be so strong as to attain stimulation of the exterior tissue such as the scalp possibly overlying the target area. The magnetic field for the real deep-stimulating effect can be induced using the same coils mentioned above or, alternatively, at least one of them. When using a plurality of coils, the stimulation is attained by feeding the coils with such varying currents that cause the electric fields induced by the coils to sum in the target area such as the brain tissue simultaneously exciting both the nerve cells of the target area and the possibly overlying tissue layer such as the scalp and the muscles associated therewith. Herein, both the real and the fake magnetic stimulation pulses can be issued without physically moving the coil or plurality of coils. Advantageously, the current pulses fed to the coils during both the fake and the real magnetic stimulation are kept essentially equal in order to maintain the sound level of the sonic bang emitted by the coils essentially unchanged during both of these stimulation operations. In a similar fashion, the invention is also applicable to the stimulation of the peripheral nervous system, muscles and spinal cord. Instead of man, a test animal for instance may be the subject of stimulation.

The response of the stimulating field on the actual target area such as the brain can be measured and assessed by subtracting the responses of the fake magnetic stimulation from those of the real magnetic stimulation.

The invention offers significant benefits.

By virtue of the invention, it is possible to issue the real and the fake magnetic stimulation pulses in an alternating manner without any need for moving or tilting the stimulator coil, thus facilitating a fast alternation of stimulation modes and keeping the position of the coil relative to the object stationary. Furthermore, the test person has no possibility of detecting a change of the stimulation mode from a movement of the coil.

In some types of conventional stimulator embodiments, the fake magnetic stimulation is achieved by moving the coil over another brain area, whereby a risk arises that the activation of a different brain area subjected to the fake magnetic pulse may affect the results of the test session. As compared with such prior-art embodiments, the present invention has the benefit of eliminating a direct effect of local stimulation on the brain and, instead, permits the direct stimulating effect of the fake magnetic pulse to be applied in a controlled and minimized manner.

In addition to these, the invention has other embodiments offering further benefits.

Advantageously, the invention can be applied using, e.g., electronic control of the stimulation current fed to the stimulator coils, whereby the operator of the stimulator can easily control the stimulator apparatus and select a desired mode of stimulation. The stimulation mode, whether the real or the fake magnetic stimulation, may be selected manually, e.g., by pressing a key or automatically in a computer-aided environment.

In a computer-aided control method of the stimulation mode, the invention may also be applied so that the stimulation mode is determined by an algorithm stored in a control computer or using a random sequence of selection, which allows an improved method of assessing the effect of magnetic stimulation applied as, e.g., a therapeutic treatment.

Figure 2:
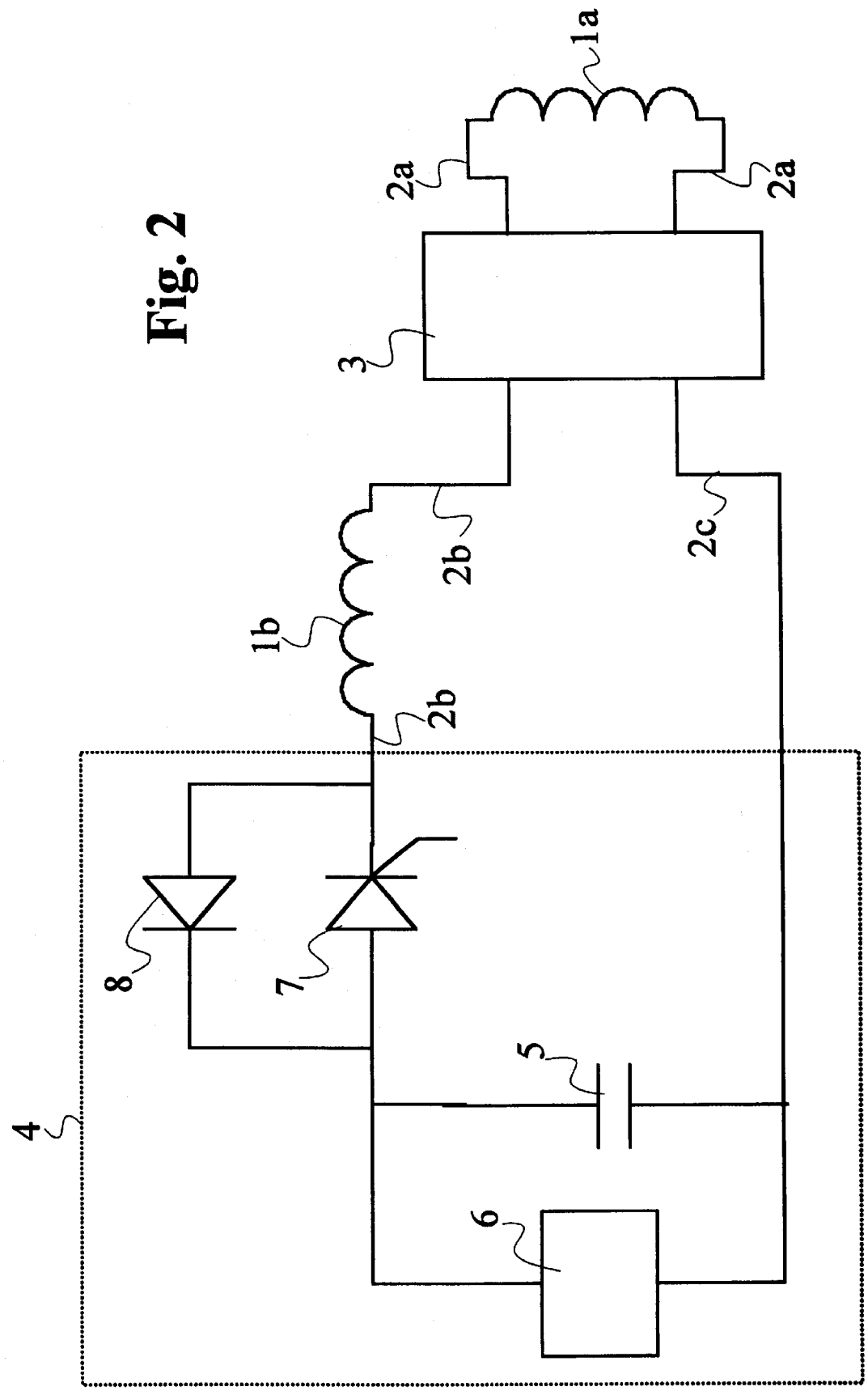

In the following, the invention will be examined in greater detail with the help of exemplifying embodiments by making reference to the appended drawings in which FIG. 1 shows the block diagram of an apparatus according to the invention suited for applying both real and fake magnetic stimulations; and FIG. 2 shows the circuit diagram of pulsing circuit suitable for use in a stimulator apparatus according to the invention.

The invention can be applied using two coils, for instance, whereby at least one of the coils is equipped with an electronic or manual selection facility of coil current polarity. When the coils are placed adjacent to each other and their currents are arranged to run in opposite directions, the electromagnetic fields produced by the coils are summed over the target area and its immediate surroundings thus causing during brain stimulation, for instance, simultaneously both the activation of the brain cells and a sensation on the scalp. By contrast, when the coils are fed with currents running in the same direction, the fields cancel each other at least partially, whereby the field strength in the target area such as the brain falls to a low level insufficient for stimulating nerve cells. However, the near field induced by the coils in their vicinity such as on the scalp remains preferably sufficiently strong to stimulate, e.g., the scalp and the underlying muscles.

The method according to the invention for producing a real magnetic stimulation effect and/or a fake magnetic stimulation effect in a biological tissue comprises the steps of:

effecting the real magnetic stimulation by virtue of inducing an electromagnetic field in a biological tissue with a sufficiently strong field strength to essentially excite said tissue, and effecting fake magnetic stimulation by virtue of inducing an electromagnetic field in the biological tissue that in the target area of said tissue is weaker than the electromagnetic field required for an essential excitation of said tissue, whereby a first electromagnetic field is induced in the biological tissue and, simultaneously, at least one second electromagnetic field is superimposed therewith having its direction deviated from the direction of said first electromagnetic field so that the sum effect of said electromagnetic fields in the target area of the biological tissue remains weaker than the electromagnetic field required for an essential excitation of the tissue.

This kind of electromagnetic field can be produced by means of a coil and its direction can be changed as required by reversing the current being fed to the coil.

In a preferred embodiment of the invention, at least two electromagnetic fields are induced in a biological tissue for producing both the real magnetic stimulation and the fake magnetic simulation. To provide the magnetic stimulation effect, the fields are induced so that their directions are oriented essentially codirectional in the target area in order to obtain a mutually augmenting effect thereof and, resultingly, to form an electromagnetic field capable of essentially exciting a biological tissue. By contrast, the generation of the fake magnetic stimulation effect is accomplished through changing the direction of at least one of the induced electromagnetic fields opposite to the codirectional field employed for producing said real magnetic stimulation, whereby at least two electromagnetic fields will be superimposed essentially in opposite directions in the target area so as to cancel the effect of each other and to produce an electromagnetic field in the target area weak enough not to essentially excite the biological tissue such as the brain.

In the preferred applications of the method, both the real and the fake magnetic stimulation are produced using essentially a single apparatus setup and essentially equal coil pulsing power levels, whereby any possible side effects associated with the real and the fake magnetic stimulation such as sensations on the scalp and an auditory response caused by the noise emissions of the apparatus remain essentially unchanged when switching between the real and the fake magnetic stimulation modes.

The apparatus shown in FIG. 1 comprises magnetic stimulator coils $1a$, $1b$ located in a parallel position close to the object being stimulated, a current source 4 feeding current to said coils $1a$, $1b$, a switch device 3 serving to reverse the current to be fed by said current source 4 in the coil $1a$, and current feed conductors $2a$, $2b$, $2c$ connecting said current source 4 to said switch device 3 and to said coils $1a$, $1b$. The switch device 3 has at least a first terminal and a second terminal for connection to the coil $1a$, a third terminal for connection to the coil $1b$ and a fourth terminal for connection to the current source. As required, the apparatus may also include a control unit adapted to control the functions of the current source 4 and the switch device 3. For simplicity, the control unit is omitted from the diagram of FIG. 1.

The conductors $2a$, $2b$, $2c$ are connected so that conductors $2a$ join the first and second terminals of the coil $1a$ to the first and second terminals of the switch device 3, the conductors $2b$ connect the first terminal of the coil $1b$ to the current source 4 and the second terminal of the coil to the third terminal of the switch device 3, and the conductor 2c connects the fourth terminal of the switch device 3 to the current source 4. Then, the switching elements of the switch device 3 can connect the conductor 2b attached to the third terminal of the switch device 3 on the conductor 2a which is connected either on the first or second terminal and, respectively, the conductor 2c leaving the fourth terminal of the switch device 3 either on the conductor 2a connected to the second or first terminal. In this manner, the coils 1a and 1b are connected in series and the current pulse fed by the current source 4 can be passed via both coils 1a, 1b so that the direction of the current via the coil 1a can be set by the switch device 3 to be either codirectional with or reverse to the current via the coil 1b. The switch device 3 may have a design permitting a connection between the third and fourth terminals, too, whereby conductors 2b and 2c can be directly connected to each other. In this circuit connection, the coil 1a is bypassed and the current pulse fed by the current source 4 is passed via the coil 1b only.

When the apparatus shown in FIG. 1 is used for inducing a magnetic field, a current pulse of 1–20 kA with a duration of 50–1000 µs is fed to the magnetic stimulator coils 1a, 1b. The current pulse is formed by a pulsing circuit comprising coils 1a, 1b, current conductors 2a, 2b, 2c, the switch device 3 and the current source 4. One possible configuration of the pulsing circuit is illustrated in greater detail in FIG. 2. The current source 4 shown in FIG. 2 comprises a capacitor 5 connected in parallel with a power supply 6 and, connected in series with these, a thyristor switch 7 paralleled with a diode 8. The current pulse is typically formed by first charging the capacitor 5 to a voltage of 0.5–4 kV by the power supply 6 and then rapidly discharging the stored energy of the capacitor 5 into the coil 1b or, alternatively, the coils 1a, 1b via the conductors 2a, 2b, 2c. In the apparatus shown in FIG. 2, the discharge of the energy storage capacitor 5 is initiated by triggering the thyristor switch 7 conductive at a desired instant of time. Prior to this, the switch device 3 is set appropriately to selected the direction of current pulse to be passed via at least one of the coils, which in the illustrated circuit is coil 1a.

Accordingly, a general function of the switch device is to connect at least one of the coils as a part of the pulsing circuit and to select the direction of the applied current pulse in at least one of the coils.

A simple type of switch device 3 based on manually connectable connectors has a switch device construction 3 comprising a first and a second connector capable of accepting a first and a second mating connector attached to the ends of the conductors 2a of the coil 1a. Hence, the direction of current to be passed via the coil 1a can be set as desired by proper interconnection of the mating connectors.

Alternatively, the switch device 3 can be implemented using, e.g., a construction with a first and a second two-position switch, a first and a second conductor wired to the first and second terminals of the coil plus a first and a second auxiliary conductor wired to said first and said second terminal of said coil. The switches, conductors and auxiliary conductors are arranged in the switch device 3 so that the first switch in its first position passes current to said first conductor of the coil and in its second position to said second auxiliary conductor, while the second switch in its first position passes current to said second conductor of the coil and in its second position to said first auxiliary conductor. Thus, the direction of the current pulse to be passed via the coil can be selected by proper setting of the switch positions. When both switches are set in their first positions thus making the above-described connections to the respective conductors, the current is passed via the coil in a first direction and when the switches are set in their second position, that is, passing the current along the auxiliary conductors, the direction of the current pulse via the coil is reversed. In a practicable construction, the switches may be solid-state switch elements or mechanical switch components.

The apparatus according to the invention may also be implemented by providing each of the coils 1a and 1b with a separate pulsing circuit. Herein, one of the pulsing circuits may operate in the same manner as the pulsing circuit shown in FIG. 2. The other pulsing circuit can be modified from the circuit configuration of FIG. 2, e.g., by replacing the diode 8 with a thyristor switch. Then, the charging polarity of the capacitor in the second pulsing circuit may be selected in a desired manner and, according to the selected charging polarity, either the first or the second thyristor switch is triggered conductive to pass the current pulse via the coil in a desired direction. This arrangement disposes with the need for a separate switch device 3 inasmuch the parallel-reverse connection of the thyristor switch elements acts as the switch device 3, whereby the direction of the applied current pulse can be selected by electrical control means. As compared with the arrangements shown in FIG. 1 or 2, the alternative arrangement with two pulsing circuits provides a further benefit of higher current pulse capacity.

Embodiments different from those described above may also be contemplated within the scope and spirit of the invention.

One alternative arrangement for producing fake magnetic stimulation can be realized, e.g., using two magnetic stimulators each having a single stimulator coil. The coils are placed adjacent to each other on the test object. Then, the fake stimulation is delivered by mechanically reorienting one of the coils by 180°, whereby the directions of the electromagnetic fields act opposite to each other. However, this technique of alternating between the fake and the real magnetic stimulation is extremely clumsy.

Another alternative technique is to use one magnetic stimulator having a separate fake stimulator coil connected thereto during the administration of the fake stimulation. Advantageously, the fake stimulator coil has an external construction identical to that of the actual stimulator coil but, however, having an internal design capable of inducing the field pattern required for fake stimulation.

Also a figure-of-eight coil can be used for producing the fake stimulation field, whereby the closed coil housing contains two coils, one of which being equipped with an optional selection of coil current direction.

In a still another alternative method, the coil currents are varied in proportion to each other during the test session from the values producing a real magnetic stimulation stepwise toward a fake stimulation and back. A benefit of this technique is that the field strength induced in the brain tissue, for instance, can be changed in a varying manner without causing an essential variation in the sensory or auditory sensation experienced by the test object.

What is claimed is:

1. A method for producing a real magnetic stimulation effect and a fake magnetic stimulation effect in a biological tissue, comprising:
   providing an electromagnetic means for inducing at least two electromagnetic fields in said biological tissue,
   in a real magnetic stimulation mode, energizing the electromagnetic means with predetermined pulsing power levels for simultaneously inducing in said biological tissue at least two electromagnetic fields oriented essentially codirectional with each other in a target area in order to obtain a mutually augmenting effect and to form a resultant electromagnetic field of sufficient magnitude for essentially exciting said biological tissue, and in a fake magnetic stimulation mode, energizing the electromagnetic means with substantially the same pulsing power levels as employed in the real magnetic stimulation mode for simultaneously inducing in said biological tissue at least first and second electromagnetic fields superimposed with each other and oriented with respect to each other in said target area in order to obtain a mutually cancelling effect and to form a resultant electromagnetic field of substantially lower magnitude than the resultant electromagnetic field formed in the real magnetic stimulation mode.

2. A method according to claim 1, comprising providing coils for inducing said electromagnetic fields.

3. A method according to claim 2, comprising maintaining said coils in substantially the same relative positions in the real stimulation mode and the fake stimulation mode.

4. A method according to claim 1, comprising providing first and second coils for inducing said first and second electromagnetic fields respectively and energizing the first coil with a first polarity in the real stimulation mode and energizing the first coil with a second polarity, opposite the first polarity, in the fake stimulation mode.

5. A method according to claim 4, comprising administering a succession of stimulation pulses in the real stimulation mode and a succession of stimulation pulses in the fake stimulation mode, and switching between the real stimulation mode and the fake stimulation mode at random or in accordance with a predetermined program.

6. A method according to claim 5, comprising switching between the real stimulation mode and the fake stimulation mode by reversing the polarity of energization of the first coil using a manually operated switch or a switch operating under control of a computer programmed to implement a predetermined test session.

7. A method according to claim 1, comprising administering a succession of stimulation pulses in the real stimulation mode and a succession of stimulation pulses in the fake stimulation mode, and switching between the real stimulation mode and the fake stimulation mode at random or in accordance with a predetermined program.

8. A method according to claim 1, comprising providing first and second separate magnetic stimulation apparatuses to generate said first and second electromagnetic fields respectively.

9. A method for producing a real magnetic stimulation effect and a fake magnetic stimulation effect in a biological tissue, comprising;

providing a first electromagnetic means for inducing a first electromagnetic field in said biological tissue, providing a second electromagnetic means for inducing a second electromagnetic field in said biological tissue, in a real magnetic stimulation mode, energizing the first and second electromagnetic means with predetermined pulsing power levels for simultaneously inducing said first and second electromagnetic fields with essentially codirectional orientation in a target region of the biological tissue in order to obtain a mutually augmenting effect and to form a resultant electromagnetic field of sufficient magnitude for essentially exciting said biological tissue, and in a fake magnetic stimulation mode, energizing the first and second electromagnetic means with substantially the same pulsing power levels as in the real magnetic stimulation mode for simultaneously inducing said first and second electromagnetic fields with such relative orientations in said target region as to obtain a mutually cancelling effect and to form a resultant electromagnetic field of substantially lower magnitude than the resultant electromagnetic field formed in the real magnetic stimulation mode.

10. A method according to claim 9, comprising providing first and second electromagnetic coils for inducing said first and second electromagnetic fields.

11. A method according to claim 10, comprising maintaining said first and second coils in substantially the same relative positions in the real stimulation mode and the fake stimulation mode.

12. A method according to claim 9, comprising energizing the first coil with a first polarity in the real stimulation mode and energizing the first coil with a second polarity, opposite the first polarity, in the fake stimulation mode.

13. A method according to claim 12, comprising administering a succession of stimulation pulses in the real stimulation mode and a succession of stimulation pulses in the fake stimulation mode, and switching between the real stimulation mode and the fake stimulation mode at random or in accordance with a predetermined program.

14. A method according to claim 13, comprising switching between the real stimulation mode and the fake stimulation mode by reversing the polarity of energization of the first coil using a manually operated switch or a switch operating under control of a computer programmed to implement a predetermined test session.

15. A method according to claim 9, comprising administering a succession of stimulation pulses in the real stimulation mode and a succession of stimulation pulses in the fake stimulation mode, and switching between the real stimulation mode and the fake stimulation mode at random or in accordance with a predetermined program.

* * * * *